US008916742B2

(12) United States Patent
Smith

(10) Patent No.: US 8,916,742 B2
(45) Date of Patent: Dec. 23, 2014

(54) ANATOMICALLY ENGINEERED CONFIGURED ARTICLE

(76) Inventor: Joseph O. Smith, Wellington, FL (US)

( * ) Notice: Subject to any disclaimer, the term of this patent is extended or adjusted under 35 U.S.C. 154(b) by 404 days.

(21) Appl. No.: 12/943,251

(22) Filed: Nov. 10, 2010

(65) Prior Publication Data
US 2012/0136313 A1    May 31, 2012

(51) Int. Cl.
*A61F 5/00* (2006.01)
*A61F 13/00* (2006.01)

(52) U.S. Cl.
USPC ............ 602/53; 602/41; 602/18; 602/19; 602/60

(58) Field of Classification Search
USPC ........ 604/304–308, 179, 180; 602/41, 42, 46, 602/48, 52, 60–66, 55, 57–59, 53, 18, 19; D24/189–192
See application file for complete search history.

(56) References Cited

U.S. PATENT DOCUMENTS

| | | | |
|---|---|---|---|
| 2,918,062 A * | 12/1959 | Scholl | 128/894 |
| 3,490,448 A | 1/1970 | Grubb | |
| 5,554,105 A | 9/1996 | Taylor | |
| 6,250,048 B1 * | 6/2001 | Linkiewicz | 53/451 |
| 6,776,769 B2 | 8/2004 | Smith | |
| 6,812,375 B2 | 11/2004 | Dennis et al. | |
| 7,393,522 B2 * | 7/2008 | Najafi et al. | 424/78.04 |
| 2008/0021361 A1 * | 1/2008 | Smith | 602/61 |
| 2010/0076362 A1 * | 3/2010 | Utterberg et al. | 602/43 |

FOREIGN PATENT DOCUMENTS

GB    2147811 A * 5/1985

* cited by examiner

*Primary Examiner* — Kim M Lewis
(74) *Attorney, Agent, or Firm* — Mark Levy; Hinman, Howard & Kattell, LLP

(57) ABSTRACT

An engineered designed article providing multi-directional support. Portions of three or more overlapping, circular-like bodies are integrated on a flexible planar membrane into products, such as bandages, headgear, tool handles, lumbar pillows, backpacks, cervical supports, and back supports, to offer a multi-directional, (360° quadrant) support or pressure-concentrating area, to enhance specific support at the medial, lateral, inferior and/or superior part of a body part. The article can be made of material that is waterproof, acts as a shock absorber, and provides multi-directional support. Medicaments can be infused into the pressure-concentrating area of the support or into the membrane itself. An aperture for accepting IV needles is also provided.

9 Claims, 6 Drawing Sheets

ANATOMICALLY ENGINEERED CONFIGURED ARTICLE

RELATED APPLICATION

This application is related to U.S. patent application Ser. No. 11/489,048, abandoned Jul. 19, 2006. This application is also related to U.S. Pat. No. 6,776,769, and incorporates he teachings thereof.

FIELD OF THE INVENTION

This invention relates to articles of manufacture primarily for bandages/wound care, ergonomic and/or orthopedic support, seating, head protection, backpack protection for support and comfort and, more particularly, to an article to protect a joint and/or a body part on a living body.

BACKGROUND OF THE INVENTION

Infection, cuts, lacerations, puncture wounds, strains, contusions, bruises, degenerative joint diseases, arthritis, and arthroscopic operations often injure the human body. Such injuries may cause infections, hematomas and inflamed areas that must be treated by bandages, taping, medication, surgery, ergonomic/orthopedic support and/or therapy. Some injuries may cause head or brain injury and/or injury to other parts of the body.

Wound care bandages have offered minimal protection to the body, since they are not designed to seal out infection, help release exudates, re-medicate, cleanse, provide cushioning, provide lab readings of infective processes or conform to or move with the body. Conventional bandages may allow infection to complicate the wound healing process. Often these complications can lead to much more severe injury or death.

In some cases, it has been found advantageous to apply a compress to the injured area to effect more rapid healing, or to prevent any further inflammation or injury. Typically, bandage support for the body is provided with square or rectangular bandages which fail to offer support, protection, or comfort and in many cases allow further infection or prematurely fall off. The conventional orthopedic or ergonomic support or bandage wrap offers no more support in the area of focus than in the areas of non-focus unless they have a stay, strap and/or hole, or they depend on the material they are made of rather than the design that offers little functionality. When protecting the body, ergonomic/orthopedic products, uniforms, apparel (pants, shorts, bras, helmets/headgear, shoes, seating design, gloves, footwear, wound care bandages, pillows, grips on tools, sports equipment and medical equipment have been made with little attention to engineered design, relying instead primarily on material.

What is needed is an anatomically engineered, configured design that represents an improvement to conventional design and that can be integrated with elastic-like material to create a better device for different products in numerous applications. It would therefore be advantageous to provide a device that offers more support, comfort, and protection and, in wound care, bandages that offer better adhesion properties and drainage due to symmetrical integrated overlapping circles. The article should conform better to body movement, have broader and more uniform adhesive borders, and provide dermal delivery of ingredients on or into the skin or body, aiding in wound healing.

This device could be held or worn as a grip and as a protective support. When utilized in different products and applications the device should also provide support, comfort, protection and/or pressure integrated into a therapeutic device for treating any living body. The device, utilized in different products and applications, should also provide support, comfort and protection integrated into a grip-like handle that may minimize slippage. In fact the device should be usable in conjunction with various mechanical and biological features including but not limited to back, full body brace, wrist, ankle, elbow, postural support, knee, uniforms, pants, shorts, helmets, shoes, seating, gloves, footwear, bandages/wound care, pillows, tools, sports equipment and medical equipment. In the preferred embodiments the device should comprise an engineered, anatomically configured design of overlapping integrated circular like bodies having concentrated pressure support for a joint and/or body part or on a product held or used by the body.

This advanced, inventive wound care article should have a cap or opening in the center to release exudates built up at the site of the wound. Such a design should allow for cleaning, IV tubing, re-medicating or alternative uses that conventional bandages do not permit. A peelable membrane or faux cover over the cap or as a replacement therefore can be used to protect the opening from bacteria and other contaminants. The wound care or orthopedic/ergonomic products that could utilize such a design should help absorb impact and deflect force to minimize injuries to the user. The wound care products could comprise foam or other material to minimize the risk of injury in either post-surgical care or, in sports, to prevent injuries.

DISCUSSION OF THE PRIOR ART

A number of patents disclose various ergonomic/orthopedic and wound care devices for support or treatment of a weakened and/or injured joint or wound.

U.S. Pat. No. 3,490,448, issued to Grubb on Jan. 20, 1970 for ADHESIVE PRESSURE PAD, discloses a removable protective strip which covers only a portion of one flap of an adhesive bandage while another longer strip contacts the opposite flap, extends across a sterile pad and releasably adheres to the remainder of the first flap. The strips terminate in pull tab portions at their junction. A procedure for inserting and removing a needle from the body includes the steps of adhering one flap of the bandage transverse to the line of insertion of the needle, while maintaining the other flap and the pad covered with the longer protection strip, inserting the needle, exposing the second flap and pad, removing the needle while pressing the pad over the puncture, and adhering the second flap to the skin with sufficient pressure to minimize bleeding.

U.S. Pat. No. 5,554,105, issued to Taylor on Sep. 10, 1996 for PATELLA STABILIZER, discloses a stabilizer that has a sleeve to be received around a knee of a wearer. A support in the sleeve has a first member to extend from beneath the wearer's patella to a point over the wearer's tibia. Bifurcated members extend from the first member along each side of the patella when the patella stabilizer is in position on the wearer. A strap extends around the wearer's leg, over the first member of the stabilizer.

U.S. Pat. No. 6,776,769, issued to Smith on Aug. 17, 2004 for ANATOMICALLY CONFIGURED TUBULAR BODY OF WOVEN OR KNITTED FABRIC FOR PRESSURE SUPPORT OF ARTICULATING JOINT, discloses an anatomically configured tubular body or ribbon of woven or knitted elastomeric yarn having concentrated pressure support means at one or more areas along said device for pressure support of an ankle, elbow, knee or wrist (hereinafter also "articulating appendage"). The device can include an anatomically configured tubular composite comprising an essentially uniform sleeve of elastomeric yarn and a pressure concentrating means corresponding to one or more areas of said articulating appendage (hereafter also "pressure points"), so as to focus or concentrate pressure support at said pressure points. The device thus provides for both ease of attachment to the appendage and of application of differential (increased or focused) pressures to a pressure point of the affected appendage.

U.S. Pat. No. 6,812,375, issued to Dennis et al. on Nov. 2, 2004 for PRESSURE-EVENIZING LOW-REBOUND WOUND DRESSING, discloses a topographically self-stabilizing, dynamic pressure-evenizing, pressure-applying, anatomical dressing which includes a pressure-applying, acceleration-rate-sensitive, temperature and pressure responsive cushioning layer which responds during a bandaging situation, both statically and dynamically, to maintain relatively uniform all-over pressure beneath it, and against the surface of a site, such as a surgical wound site.

It is an object of this invention to remedy the above as well as related deficiencies in the prior art.

More specifically, it is a principal object of the present invention to provide an anatomically engineered configured article of 720 degrees for pressure support of wounds of a joint and/or body part, by integrating this article into a wound care/bandage or as a preventive for sports or medicine, orthopedic/ergonomic support, apparel (uniforms, pants, shorts), helmet, headgear, shoes, seating design, gloves, footwear pillows, tools, sports equipment and medical equipment.

It is another object of this invention to provide an anatomically engineered configured article made up of three or four integrated overlapping circular-like bodies or portions thereof for pressure support, protection, absorption and deflection of pressure of any body part, which may provide support inferior, superior, medial and and/or lateral. This article can provide negative pressure.

It is yet another object of this invention to provide an anatomically engineered configured article comprising three or four integrated overlapping circular-like bodies or portions thereof or membrane of material that could be used as bandages (wound care), orthopedic/ergonomic support, in apparel, helmets, shoes, seating design, gloves, footwear, pillows, tools, sports equipment and medical equipment for concentrated pressure support of a joint and/or body part with a multi-directional 360° quadrant support.

SUMMARY OF THE INVENTION

The above and related objects are achieved by providing a membrane/support device made of overlapping integrated circular-like bodies or portions thereof that provide a multi-directional support and give an enhanced 360° quadrant support over or in relation to any body part. The device can include an anatomically engineered, configured device comprising three, four, or more overlapping, integrated circular-like bodies. These integrated circular-like bodies provide a pressure concentrating means corresponding to one or more areas of a body part. The resulting multi-directional (360° quadrant) support, hereafter also referred to as "pressure points," allows the article to focus or concentrate pressure support at the inferior, superior, medial and lateral points. The device thus provides for both ease of attachment to another product to increase or focus pressure at the joint and/or any body-fitted part to minimize outside pressure and/or impact, or to act separately, which can result in better protection and can decrease the chance of injury.

In the preferred embodiment of this invention, the pressure concentrating means of the composite engineered device comprises a delimited area having a plurality of integrated overlapping rings or portions of rings of materials. The integrated overlapping rings result in relatively greater support than that of the product or material alone. For example, in wound care this engineered device provides better adhesion, protection, support and comfort and moves and conforms with the body to enable better drainage. In addition, a cap or opening that may be in the center can allow dermal delivery of pharmaceuticals. The application of the material design can also be for synthetic skin. A laboratory testing strip or chip can be placed in this wound care device that can react and tell the type of infective process in a wound or opening, minimizing the infective process and aiding significantly in healing, preventing further injury and unnecessary related costs. The engineered wound care device can comprise protein or other material that is either absorbed or disintegrates in the course of fulfilling its task without necessarily being removed.

In addition, in the case of a helmet/headgear for support of the head, the areas with the pressure concentrating means can be located at several locations acting individually and/or jointly. The integrated overlapping rings act as shock absorbing units that can reduce impact and deflect force upon impact.

In the seating system, the design absorbs and deflects impact to minimize the potential insult to both the pelvis and the spine.

In an adhesive bandage, the integrated circular like bodies provide 720 degrees, of support to offer better comfort, support, protection and adhesion, significantly better compared with other geometric designs.

In a grip of a handle of a tool, medical instrument, sports equipment, weaponry, etc., the multi-directional support offers better comfort, support, protection and/or control.

In a lumbar pillow for seating support, the multi-directional support provided by the overlapping integrated circular-like bodies offers an opportunity for better comfort, support, protection and/or control when used for orthopedic/ergonomic support. This design offers excellent stability.

BRIEF DESCRIPTION OF THE DRAWINGS

Various objects, features, and attendant advantages of the present invention will become more fully appreciated as the same becomes better understood when considered in conjunction with the accompanying drawings, in which like reference characters designate the same or similar parts throughout the several views, and wherein.

DETAILED DESCRIPTION OF THE INVENTION

The figures that accompany this application and referenced herein depict representative embodiments of the engineered device of this invention used in various wound care environments and related ergonomic/orthopedic applications. In each instance, the composite may comprise a layer of material with three or more overlapping, integrated, circular-like bodies or portions thereof providing a multi-directional, 360° quadrant support having concentrated pressure support means arranged at pre-designated locations. The articles include, but are not limited to, bandages/wound care and related orthopedic/ergonomic care, apparel (uniforms, pants, shorts), helmets, headgear, shoes, seating design, gloves, footwear, pillows, tools, sports equipment and medical equipment. The engineered design material can be anatomically configured onto a particular product or at a particular location providing a multi-directional, 360° quadrant support within the product or independent in one or multiple locations providing negative pressure (i.e., a partial vacuum providing suction under the bandage 10, drawing bacteria and fluid away from the wound). Four quadrants, each comprising 180° of support, may also be considered 720° of support.

Figure 1A:
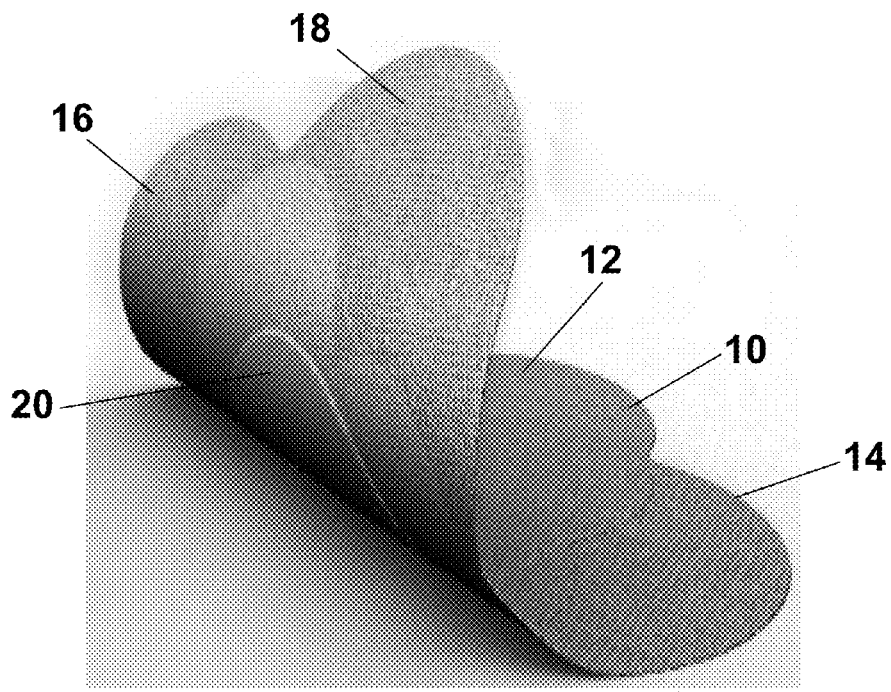
FIG. 1a is a perspective view of an adhesive bandage and support device of this invention.

FIG. 1a is a view of a device 10 of the invention shown bent to illustrate the elements of device 10. Portions of four overlapping, integrated, circular-like bodies 12, 14, 16, 18 are provided and are suitable for support of an adhesive bandage. It should be understood that as few as three and as many as five or more bodies can be used in order to focus pressure to the central portion 20 or integrated into the lower surface thereof. The device 10, which can be substantially clear, can have various materials at the lower surface of central portion 20 thereof. Such materials include, but are not limited to integrated antibiotic, testing strip or chip, hydrogel, hydrocolloid, analgesic, foam, silicon, etc. to treat injury, disease and infection or provide comfort and support. The material at the central portion 20 can either be absorbed by the body or can disintegrate in several days after it does its job. Such absorbable material may include, but not be limited to absorbable gelatin; while disintegratable material may include, but not be limited to copolymer starch and/or thermoplastic starch.

Figure 1B:
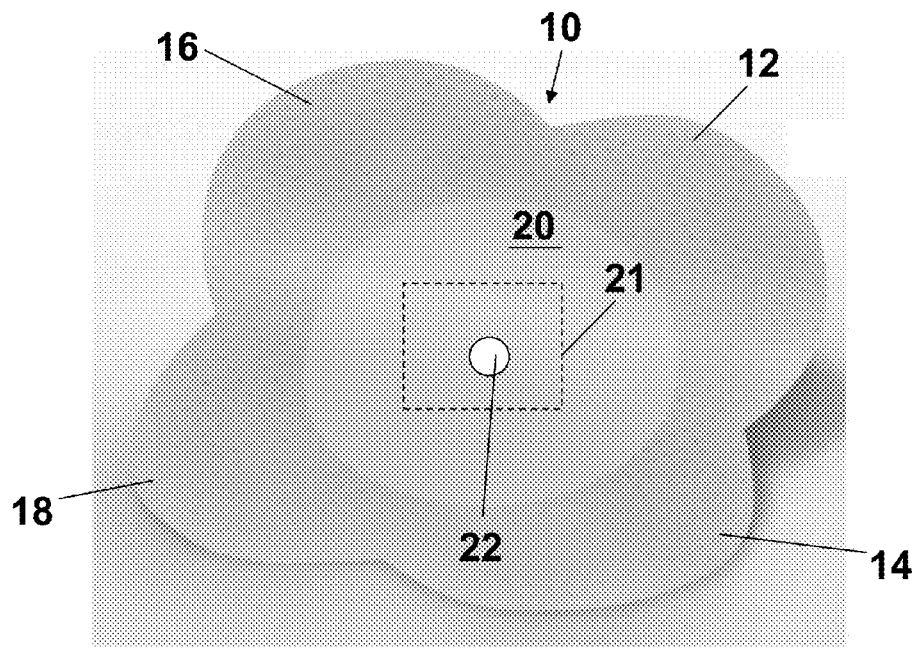
FIG. 1b is a perspective view of a wound care bandage with a cap or hole disposed, for example, in the center thereof.

Referring to FIG. 1b, there is shown a bandage 10 with a cap or hole 22 for intravenous (IV), medication, not shown, and release of exudates. A faux cover or peelable membrane 21 can be placed above the hole 22 in order to prevent bacteria or other contaminants from entering hole 22. Although cap or hole 22 is shown in FIG. 1b as extending through central portion 20 and disposed at the center thereof, more than one hole 22 can be provided and can be disposed at any location(s) in central portion 20.

Figure 1C:
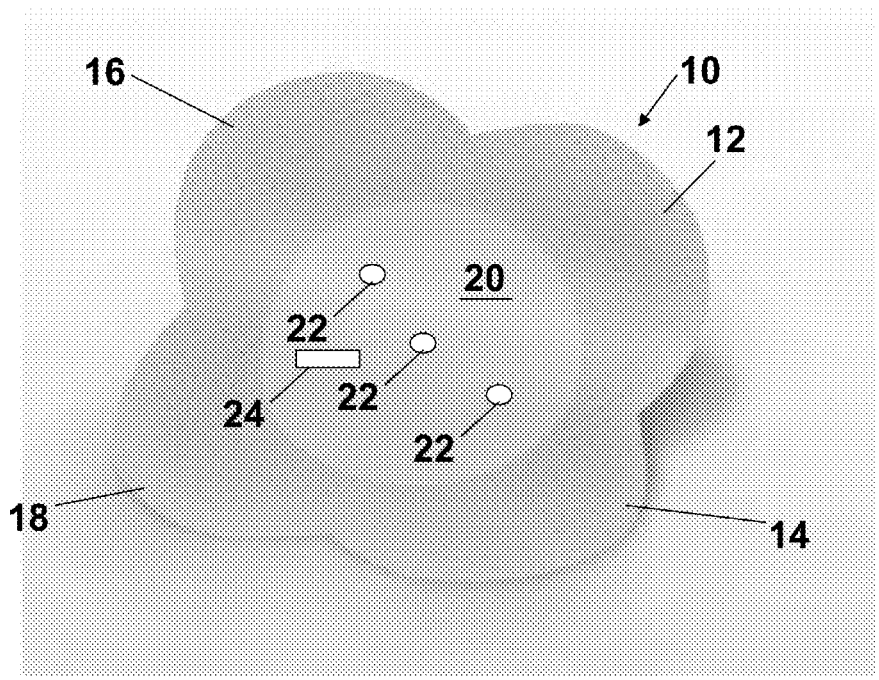
FIG. 1c is a perspective view of a bandage with a central core or portion for dispensing medication or ingredients into a body.

Referring to FIG. 1c, bandages 10 can dermal deliver medication centrally 20 or throughout bandage 10. Moreover, any number of holes 22 can be placed through the central portion 20 of device 10, as shown. Moreover, a laboratory strip or chip 24, well known in the art, can visually indicate the state of infection of a wound.

Figure 2A:
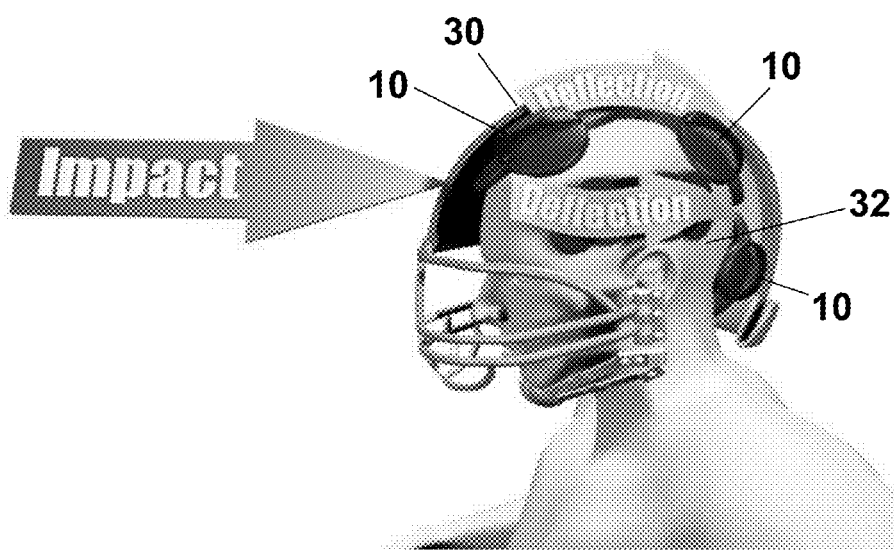
FIG. 2a is a perspective view of a helmet with the support device of this invention showing how force is absorbed and deflected upon impact.
Figure 2B:
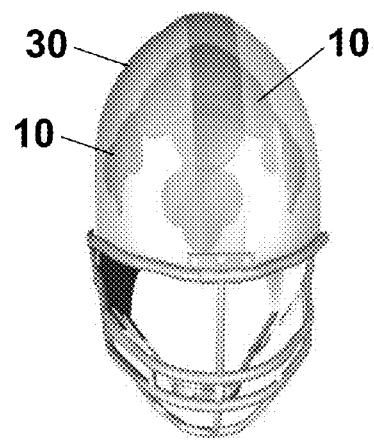
FIG. 2b is a symmetrical view of a helmet in which inserts are placed to minimize head and brain injury.

Similarly, in FIGS. 2a and 2b, the device 10 is preconfigured in an anatomical shape suitable as a head design support.

The device 10 can be organized and integrated for headgear 30 where the device 10 acts as an individual joint shock absorber, minimizing impact, shock, vibration and force to head or brain Reference numeral 32 represents three integrated, circular bodies providing multi-directional support to deflect impact in the temporal area of a head to minimize injury.

Figure 3:
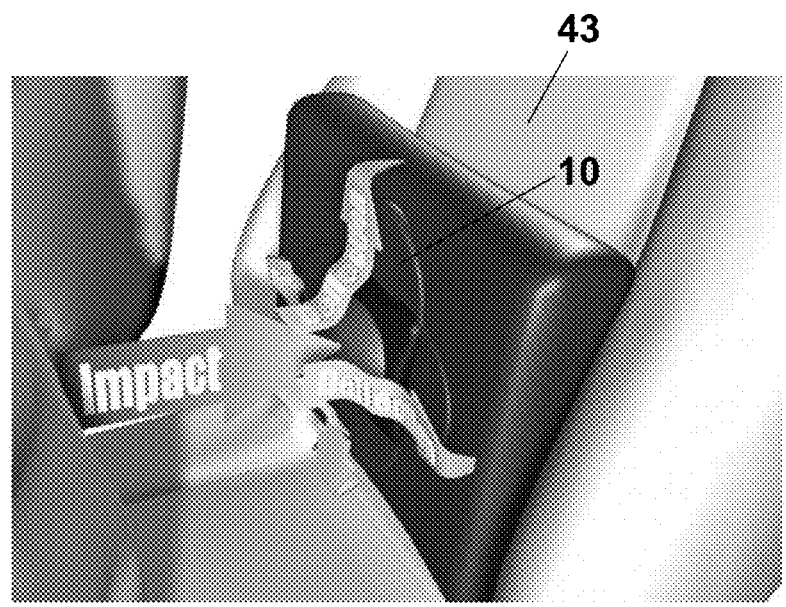
FIG. 3 is a perspective view of a seating design with the inventive device integrated therein.

Referring now to FIG. 3, another view is provided for the device 10 configured in an anatomical shape suitable as a lumbar support. The device 10 of this invention can also be configured in an anatomical shape suitable as a lumbar support that can be integrated into seating in vehicles, chairs, benches, or furniture. In FIG. 3, a lumbar pillow is shown integrated into seating 43 so that, upon impact or pressure, this device absorbs, distributes and deflects the force.

Figure 4:
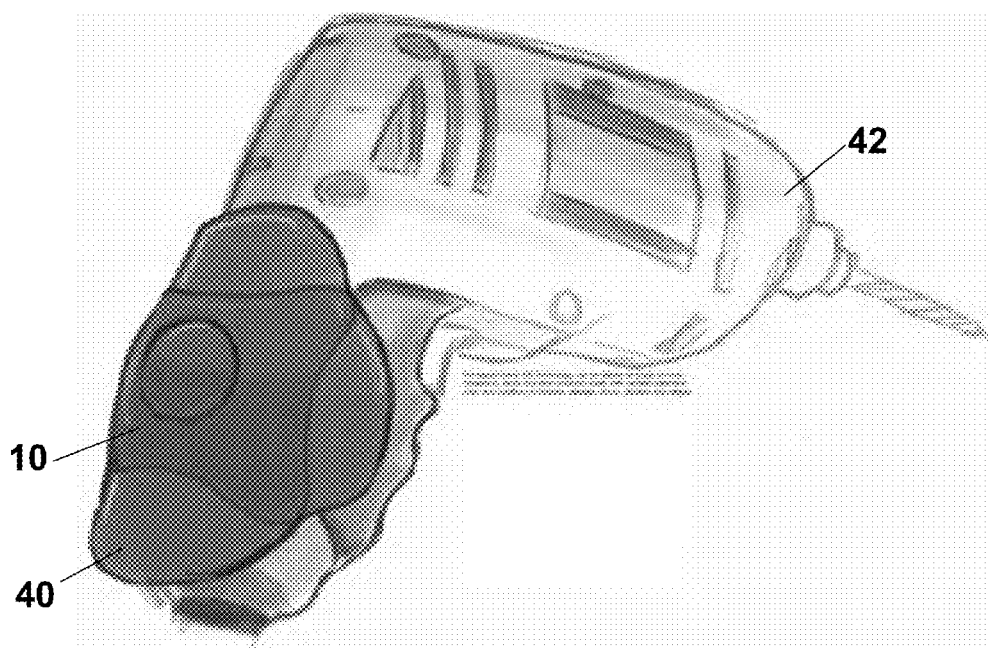
FIG. 4 is a perspective view of a tool with a support device of this invention.

Referring to FIG. 4, device 10 is illustrated as a portion of a grip 40 on a power tool 42 offering multi-directional support. The tool grip 40 minimizes slippage and absorbs and deflects vibration and shock for the user from tool 42.

Figure 5:
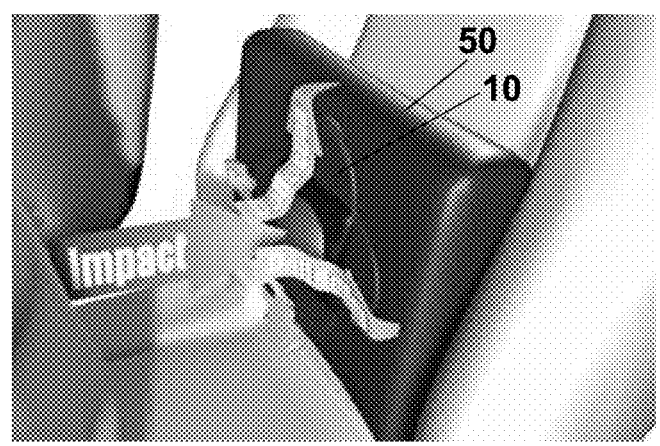
FIG. 5 is a perspective view of a lumbar pillow with the support device of this invention.

Referring to FIG. 5, there is illustrated device 10 incorporated into a lumbar support pillow 50 that offers spinal support as we as medial and lateral muscle support. In a lumbar support pillow, spinal support as well as medial and lateral muscle support are provided. The device 10 is configured in an anatomical shape suitable as a lumbar support when seated. The pillow absorbs, distributes and deflects the force upon impact or pressure.

Figure 6:
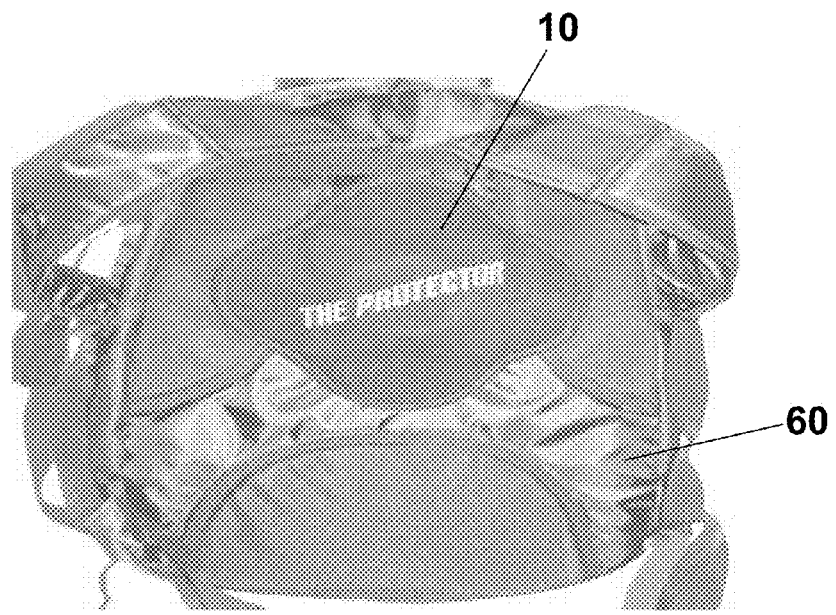
FIG. 6 is a perspective view of a backpack with design material with the support device of this invention.

Referring to FIG. 6, there is illustrated device 10 incorporated into a backpack 60. The insert, material design offers excellent support, protection and performance, minimizing pressure and injury to the user's spine.

Figure 7:
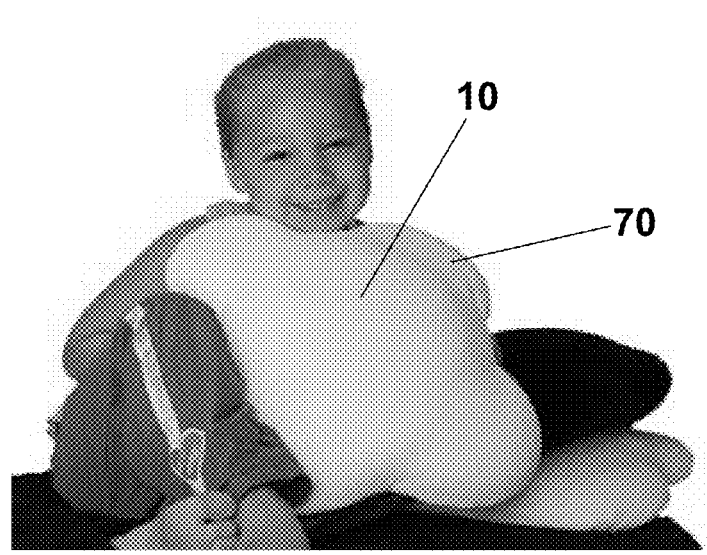
FIG. 7 is a perspective view of a cervical/lumbar apparatus with design material with the support device of this invention.

Referring now to FIG. 7, there is shown a cervical/lumbar pillow 70 incorporating a larger device 10 and offering protection, support and comfort in both the cervical and lumbar spine.

Figure 8:
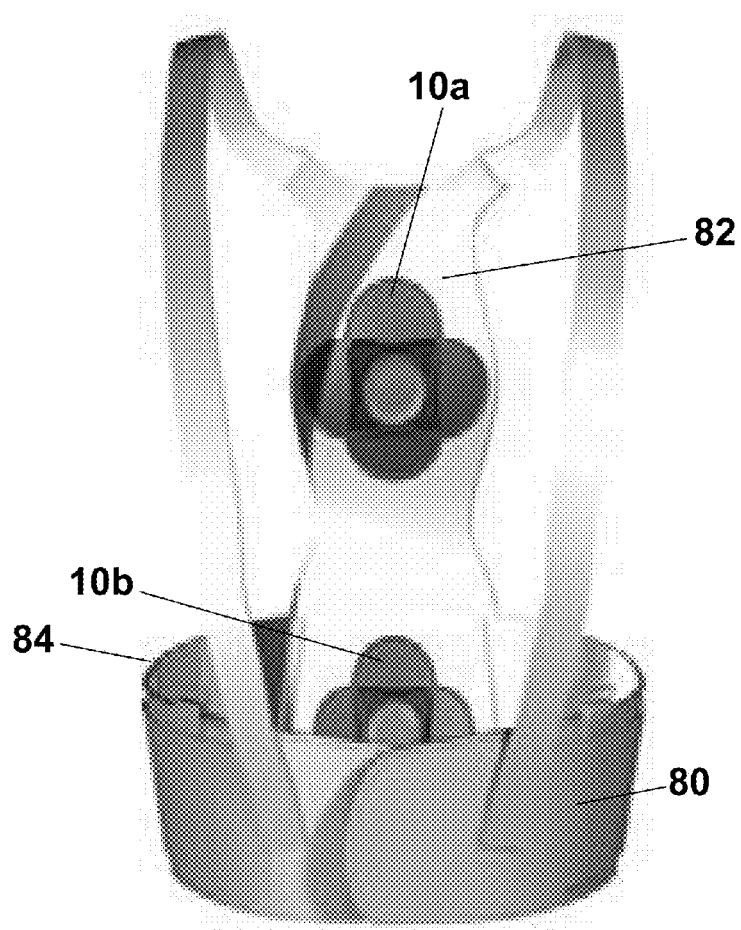
FIG. 8 is a perspective view of a back support with a design material with the support device of this invention.

Referring now to FIG. 8, there is shown a back support 80 incorporating devices 10, where the material design or inserts offer multi-directional comfort, protection and support to the upper back (device 10a) as well as the lower back (device 10b). The devices 10a, 10b may be movable or be fixed. The upper and lower supports 82, 84 can be separated from one another.

Since other modifications and changes varied to fit particular operating requirements and environments will be apparent to those skilled in the art, the invention is not considered limited to the example chosen for purposes of disclosure, and covers all changes and modifications which do not constitute departures from the true spirit and scope of this invention.

Having thus described the invention, what is desired to be protected by Letters Patent is presented in the subsequently appended claims.

What is claimed:

1. In an engineered designed article for pressure support that is anatomically configured to fit, support and protect a body part, the improvement comprising: portions of at least three integrated, combined elements shaped as portions of circles to form positive or negative pressure-concentrating means on at least one predetermined area of said body part, said portions of at least three integrated, combined elements shaped as portions of circles providing enhanced 360° quadrant to support at least one location; and a plurality of caps or holes extending through a central portion of said pressure-concentrating means for permitting intravenous tubing, medicaments and release of exudates therethrough.

2. The article of claim 1, wherein said engineered designed article is selected from the group consisting of: bandages/ wound care, helmets, tools, sports/medical equipment, weaponry, lumbar pillows and cervical/lumbar/seating pillows.

3. The article of claim 1, wherein said pressure-concentrating means are spaced apart at predetermined locations on said article.

4. The article of claim 1 further comprising at least one medicament absorbable in a body, said medicament being disposed on at least one of the locations: at the pressure-concentrating means and anywhere on said article.

5. The article of claim 1, further comprising at least one of the group: foam, silicon, calcium alginate, hydrocolloids, hydrogels, antimicrobial agents and pharmaceuticals disposed on at least one of the locations at the pressure-concentrating means and anywhere on said membrane.

6. An anatomically configured engineered designed article comprising: a plurality of integrated circles combined to form a flexible membrane bandage, portions of at least three of said integrated circles providing enhanced 360° quadrant to support at least one location; and a plurality of caps or holes proximate said plurality of integrated circles for IV tubing, wound drainage, and medication, said plurality of caps or holes disposed through said enhanced 360° quadrant to support at least one location for permitting an intravenous article to be admitted therethrough.

7. The article of claim 6, further comprising a membrane disposed over said aperture for preventing bacteria or other contaminants from entering said aperture.

8. The article of claim 6, wherein said article is used as a substitute skin for victims.

9. The article of claim 6, wherein said bandage is substantially clear for covering wounds and allowing medication, tubes and other treatment through said aperture.

* * * * *